United States Patent [19]

Wigginton et al.

[11] Patent Number: 4,718,908

[45] Date of Patent: Jan. 12, 1988

[54] HIGH-STRENGTH, COLD-FORGED TYPE 316L STAINLESS STEEL FOR ORTHOPEDIC IMPLANT

[75] Inventors: Robert E. Wigginton, Collierville, Tenn.; Barry Gordon, Hernando, Miss.; Imogene Baswell; Steve Garner, both of Memphis, Tenn.

[73] Assignee: Richards Medical Company, Memphis, Tenn.

[21] Appl. No.: 616,659

[22] Filed: Jun. 4, 1984

[51] Int. Cl.$^4$ ................................................ A61F 5/04
[52] U.S. Cl. ........................................ 623/16; 623/23; 148/12 E; 72/700
[58] Field of Search ................ 148/12 E, 38; 72/377, 72/700; 128/92 B, 92 BA, 92 BB, 92 BC, 92 D; 3/1.9; 75/128 R; 623/16, 23

[56] References Cited

U.S. PATENT DOCUMENTS

| | | | |
|---|---|---|---|
| 2,358,799 | 9/1944 | Franks | 148/12 E |
| 3,100,729 | 8/1963 | Goller | 148/38 |
| 3,284,250 | 11/1966 | Yeo et al. | 148/12 E |
| 3,340,048 | 9/1967 | Floreen | 148/38 |
| 3,740,274 | 6/1973 | Chow | 148/12 E |
| 3,871,925 | 3/1975 | Nunes | 148/12 E |
| 4,429,690 | 2/1984 | Pievani | 128/92 D |

OTHER PUBLICATIONS

*Handbook of Stainless Steels*, Peckner & Bernstein, 1977, pp. 42-6 to 42-10, "Surgical Implant Manufacturing", McGraw-Hill Co.

*Primary Examiner*—Lowell A. Larson
*Attorney, Agent, or Firm*—Pravel, Gambrell, Hewitt, Kimball & Krieger

[57] ABSTRACT

A surgical implant manufactured from austenitic stainless steel by cold-forging has improved mechanical properties and corrosion fatigue resistance. The grain-size index for the cold-forged 316L stainless steel is increased from an ASTM grain-size index of about 8 to an ASTM grain-size index of about 14 by cold-forging the steel into the desired shape. Further improvement in mechanical properties and corrosion fatigue resistance is obtained by stress relieving the material after cold-forging into the desired configuration. The microstructure of the cold-forged material is characterized by the absence of visible slip planes at 600× magnification, in contrast with visible slip planes present in the microstructure of the austenitic stainless steel starting material.

12 Claims, 12 Drawing Figures

HIGH-STRENGTH, COLD-FORGED TYPE 316L STAINLESS STEEL FOR ORTHOPEDIC IMPLANT

BACKGROUND OF THE INVENTION

This invention relates to surgical implants and, more particularly, to a method of manufacturing such implants from surgical grade austenitic stainless steel such as Type 316L stainless steel. The invention further relates to bone plates and similar implant devices made from Type 316L stainless steel.

Among the biocompatible alloys commonly used for surgical implants are (1) titanium alloys, (2) cobalt-chromium-molybdenum-carbon alloys and (3) austenitic stainless steel alloys, the later also known as the 300 series stainless steel.

Of the 300 series stainless steels, Types 316 and 316L are the most commonly used for surgical implants. Type 316L is preferred over Type 316 for implants because of its superior corrosion resistance. Of these three major alloy groups, the titanium alloys, typically Ti-6A1-4V, are the most expensive, and they also exhibit the greatest resistance to corrosion when subjected to the highly corrosive environment of the human body under repeated loading resulting from body motion and weight.

Titanium alloys are useful for implants because they have superior corrosion resistance over other biocompatible materials. However, they have inferior wear characteristics when compared with either the cobalt-chromium-molybdenum alloys or the 300 series stainless steels. For this reason, they have not normally been used for implant which include members having a frictional interface. See Devine, T.M., The Comparative Crevice Corrosion Resistance of Co-Cr Base Surgical Implant Alloys, 123 J. Electochem Soc.: Electrochemical Sc. and Tech. No. 10, pp. 1433–1437 (Oct. 1976). Titanium alloys are also among the more expensive of the implant metals, considering both the raw material and manufacturing costs.

The wrought cobalt-chromium-molybdenum alloys have about the same tensile strength as the titanium alloys, but are generally less corrosion resistant. They also have the further disadvantage of being difficult to work thus requiring long production lead times.

The austenitic or 300 series stainless steels were developed to provide high-strength properties while maintaining workability. These steels are, however, less resistant to corrosion and hence more susceptible to corrosion fatigue than the more expensive titanium alloys and the cobalt-chromium-molybdenum-carbon alloys. Thus, although sufficiently strong for some corrosive environments, their susceptibility to corrosion fatigue has in the past limited their utility for surgical implants. More particularly, their use has in the past been limited to applications which permit the implant device to be designed for mechanical strength or where strength requirement were low to moderate. It would therefore be desirable for surgical implant applications to improve the corrosion resistance of the more workable, more wear resistant, and less expensive, austenitic stainless steels.

In the past, a small amount of cold-working has been done to austenitic stainless steels to increase their mechanical strength. The cold-worked material is then used as a starting material for the manufacture of surgical implants. Additional strength improvement has been reported for one of the austenitic steels, namely Type 316L, by subjecting the cold-worked steel to a low temperature stress relief process, as discussed in "Improved Properties of Type 316L Stainless Steel Implants by Low-Temperature Stress Relief", by Hochman, et al., Journal of Materials at 425–442 (1966). The Hochman, et al. article reports improvement in hardness, tensile strength, and yield strength by stress relieving cold-worked specimens of Type 316L stainless steel at temperatures of about 750° F. (399° C.) for approximately two hours. Although some improvement in mechanical strength of the cold-worked starting material has been achieved by this stress-relief technique, as reported by Hochman, the corrosion fatigue resistance of the stress-relieved starting material is not improved by such stress relieving.

It has also been reported that cold-working austenitic stainless steels reduces their corrosion resistance and therefore makes them more susceptible to pitting and corrosion fatigue in the generally saline environment of the human body. See, e.g. A. Cigada, et al., "Influence of Cold Plastic Deformation on Critical Pitting Potential of AISI 316L Steels in an Artificial Physiological Solution Simulating the Aggressiveness of the Human Body", J. Biomed. Mater. Res. 503 (1977); R.S. Brown, "The Three-Way Tradeoff in Stainless-Steel Selection", Journal of Mechanical Engineering, Nov., 1982, p. 59; and B. Syrett, et al., "Pitting Resistance of New and Conventional Orthopedic Implant Materials - Effect of Metallurgical Corrosion", Vol. 34, No. 4, pp. 138–145 at p. 144 (April 1978). These conclusions appear to be based on corrosion tests of samples of the starting material which had been nominally cold-worked for the purpose of improving its tensile strength over that of the annealed starting material.

Because of the general belief that cold-working would be detrimental to corrosion resistance, implants from austenitic stainless steels such as Type 316L have previously been formed by the process of hot forging. It is generally known that hot forging or heat treating austenitic stainless steels in contrast with the titanium alloys does not improve their tensile strength, although it may slightly improve their corrosion characteristics. Thus the finished implant produced by hot forging did not normally exhibit properties substantially different from the starting material. In addition, fabrication by hot forging is more time consuming and expensive than cold-forging fabrication techniques.

It would therefore be advantageous to provide an inexpensive manufacturing technique for forming implants from the less expensive and better wearing austenitic stainless steels such as Type 316L. It would also be advantageous to improve their resistance to corrosion fatigue to permit their use in a wider range of implant devices than has heretofore been possible.

SUMMARY OF THE INVENTION

The invention relates to a method of manufacturing surgical implants from austenitic stainless steel which improves both the mechanical strength and corrosion fatigue resistance of such steels. The invention includes forming the implant device by cold-forging the starting material. In a preferred embodiment, after cold-forging, the formed implant is stress relieved at temperatures of about 750° F. (399° C.) for about two hours. It has been found that cold-forging the starting material in the process of manufacturing an implant device causes a change in the microstructure of the starting material which results in significant improvements in both mechanical strength and corrosion fatigue resistance. In particular, although small amounts of cold-working such as the amounts normally used to increase tensile strength of the annealed starting material may somewhat lessen its resistance to corrosion fatigue, cold-forging the starting material to form an implant device was found to improve resistance of the material to corrosion fatigue.

The cold-forged steel includes a microstructure different from the "cold-worked" starting material. More particularly, the slip planes observable at 600× magnification in the "cold-worked" starting material are not found at the same magnification in the "cold-forged" steel of the instant invention. (The definitional difference between "cold-worked" and "cold-forged" for the purpose of the subject invention are discussed in greater detail below.) In addition, the cold-forged steel is characterized by an ASTM grain-size index about 14 or above compared to an ASTM grain/size index of about 8 for the starting material. The smaller grain size (equivalent to a high ASTM grain-size index) results in a material with good mechanical strength in addition to its improved corrosion fatigue resistance.

In an illustrated embodiment of the cold-forging technique, a hip plate is manufactured from 11/16 inch (1.75 centimeters) in Type 316L steel bar stock which is "cold-worked" by forging, impact reducing or other rapid reduction techniques. Opposite end portions of the bar stock are reduced to the diameter of about 0.52 inches (1.32 cm), leaving an intermediate portion of the bar stock unforged; bending the forged stock about the intermediate portion to a predetermined angle; and further forging one end portion of the bent stock to a predetermined form, e.g. by pressing with a force between about 881.6 and 1102 U.S. tons (800–1000 metric tons) with a suitably shaped die. Thereafter, for further strenghtening, the formed implant is stress relieved by heating the implant to a temperature of about 750° F. (399° C.) and maintaining it at that temperature for about 2 hours, followed by ambient air cooling.

Practicing the instant invention results in a surgical implant having better strength and corrosion fatigue resistance than implants formed from 316L stainless using conventional manufacturing techniques. The implant produced was found to have significantly higher corrosion fatigue strength than either stock "cold-worked" Type 316L stainless steel or stress-relieved stock Type 316L. More particularly, the results of corrosion fatigue testing demonstrate an endurance limit for the cold-forged, stress relieved implant, which is 40% or more above previously reported endurance limits for the Type 316L stainless steel starting material. See Imam, et al, "Corrosion Fatigue of 316L Stainless Steel Co-Cr. Mo Alloy, 2nd Eli Ti-6A1-4V," ASTM STP 684, 1979. Standard testing demonstrates that the resulting implant is capable of withstanding extensive cyclic loading in a corrosive environment like that of the human body.

BRIEF DESCRIPTION OF THE DRAWINGS

A better understanding of the invention can be had when the detailed description of a preferred embodiment set forth below is considered in conjunction with the drawing in which.

DETAILED DESCRIPTION OF A PREFERRED EMBODIMENT

Referring to the drawings, a preferred embodiment of the cold-forged stainless steel of the present invention is described in detail. In the following discussion, to distinguish between cold-worked 316L stainless steel starting material and the final product formed in accordance with the subject invention, the term "cold-worked" is used to refer to the 316L stainless steel in its typical condition as a starting material as received from a supplier. On the other hand, the term "cold-forged" refers to the 316L stainless steel after it has been subjected to one or more forging steps for producing a useable shape such as, for example, a surgical implant device. Thus, the term "cold-forging" for purposes of the subject invention means any technique for transforming a piece of metal into a different configuration, below the recrystallization temperature of the metal, by hammering, rolling, drawing, extruding, pressing, swaging, bending or other working techniques.

Figure 1:
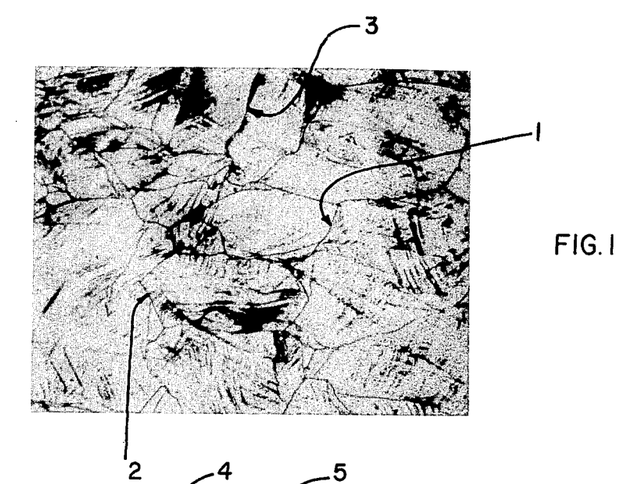
FIG. 1 is a photomicrograph at 600× magnification showing the microstructure of cold-worked Type 316L stainless steel before practicing the instant invention.
Figure 2:
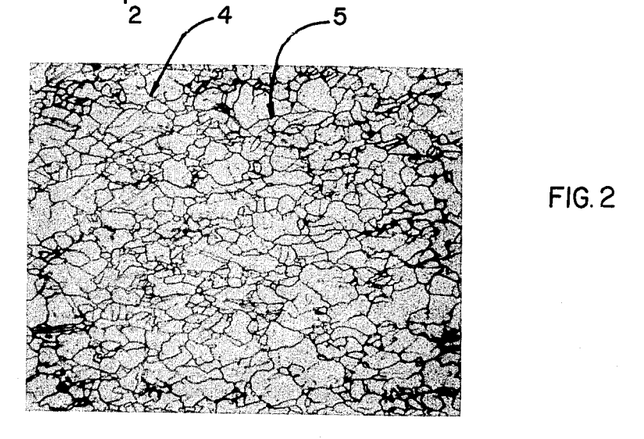
FIG. 2 is a photomicrograph at the same magnification as FIG. 1 showing the steel after a first cold-forging step in accordance with the invention.
Figure 3:
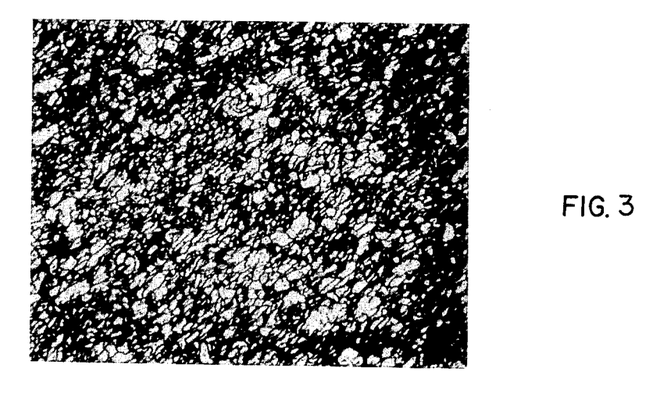
FIG. 3 is a photomicrograph at the same magnification as FIGS. 1 and 2 showing the steel after a second cold-forging step in accordance with the invention.

FIGS. 1–3 are optical microscope photomicrographs of samples of Type 316L stainless steel. The sample were mounted, ground, polished, and etched according to accepted practice using the same procedures for each sample. The electrolytic etchant used was developed to bring out the austenitic grain boundaries in the respective materials. Each figure represents a 600× magnification. The Type 316L stainless steel starting material of FIG. 1 includes parallel lines or bands, pointed out by arrows designated by reference numerals 1, 2 and 3, which reflect some cold-working of the stock material, in accordance with its manufactured designation as "cold-worked" Type 316L stainless steel. The parallel lines or bands 1-3 indicate that slip has occurred on planes of preferred orientation within the crystal lattice. The large-grained microstructure shown in FIG. 1 is typical of austenitic stainless steels in general, while the slip planes are characteristic of cold-worked austenitic steels. As noted above, the cold-worked starting material has somewhat better tensile strength than the annealed starting material.

As can be seen from FIG. 2, after a first cold-forging step discussed below, although some slip planes are still visible as pointed out by arrows designated by reference numerals 4 and 5, the material has a significantly smaller-grained microstructure than the cold-worked stock material shown in FIG. 1. FIG. 3 is a photomicrograph of the material after a second cold-forging step described in greater detail below, which shows that the slip planes of FIGS. 1 and 2 are no longer present.

Because of the highly corrosive environment to which materials used for devices implanted on the human body are subjected, such materials must be corrosion resistant in order to maintain their strength. Microscopic examination of implant devices after they have been implanted for a period of time revealed that corrosion occurs generally along the slip planes in the microstructure of the material. The absence of slip planes in the cold-forged material shown in FIG. 3 is believed to indicate a more corrosion resistant material than, for example, those shown in FIGS. 1 and 2. As discussed below, corrosion fatigue testing of the material shown in FIG. 3 confirms that the cold-forged Type 316L stainless steel is significantly more corrosion fatigue resistant than the original cold-worked material.

Using a conventional mean grain intercept method, the grain size of the starting material shown in FIG. 1 was determined to be about 8, using the standard American Society for Testing and Materials (ASTM) "grain-size index." In order to observe the grains shown in FIG. 3, because of their very small size, an oil dispersion lens with the magnification of 1500× was required. Using this magnification and the same mean grain intercept method with appropriate adjustments for the ASTM 100× standard magnification, the grain size of the cold-forged material shown in FIG. 3 was determined to be about 18 (ASTM grain-size index). It is believed that this small grain size (i.e. high ASTM grain-size index number) is the major reason for the high mechanical strength and good corrosion fatigue strength properties exhibited by the cold-forged steel of the subject invention. In addition, the absence of slip planes eliminates potential sites for stress corrosion cracking. Even with a magnification of 1000×, there were no observable slip planes in the cold-forged Type 316L steel of FIG. 3.

Figure 4:
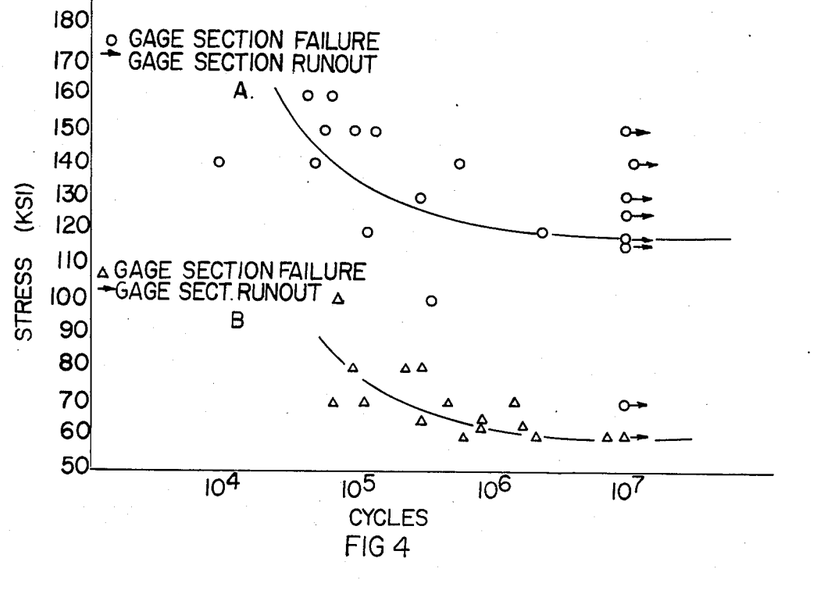
FIG. 4 is a graph showing the fatigue strength of the cold-forged material as shown in FIGS. 1 and 3, curve A showing the fatigue strength of the steel of FIG. 3 and curve B showing the fatigue strength of the steel of FIG. 1.

The fatigue strength of the material of FIG. 3 was determined by fatigue testing, after passivation, in 37% lactated Ringer's solution in a tension/tension mode. The curves shown in the graph of FIG. 4 represent a standard S/N plot of the data resulting from this corrosion fatigue testing. The curve labeled B represents the results of testing the material shown in FIG. 2, while the curve labeled A represents the results of testing the material shown in FIG. 3. As can be appreciated, the scatter of data points is typical for corrosion fatigue testing in that there are many variable factors which influence the initiation and propogation of a crack through the material. The point at which the S/N curve becomes horizontal is called the fatigue or endurance limit, below which the material can presumably endure an infinite number of cycles without failure. Thus curve A indicates an endurance limit of 120 KSI, while curve B indicates an endurance limit of 60 KSI. Thus curve A represents a 100% improvement in endurance limit over the limit for the Type 316L starting material.

Figure 5:
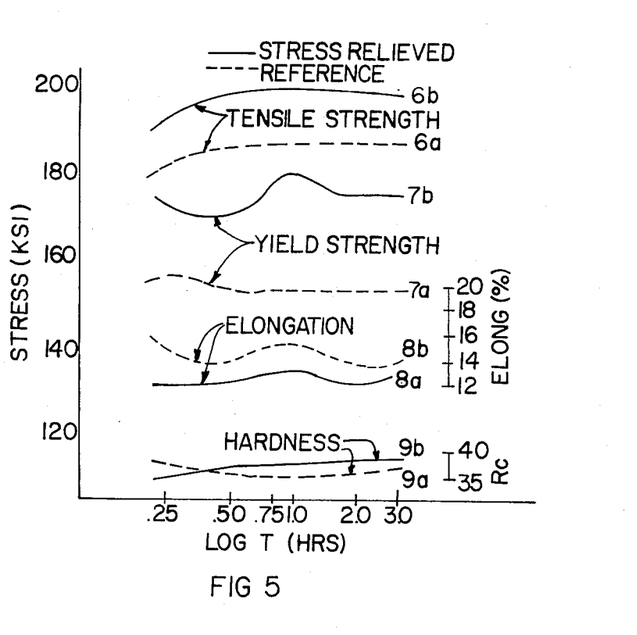
FIG. 5 is a graph showing the mechanical properties of the material of FIG. 3 in broken lines, with solid lines showing the mechanical properties after the steel has been stress relieved.

FIG. 5 illustrates conventional stress curves showing the mechanical properties of the cold-forged Type 316L of the subject invention as tested using the fatigue testing technique noted above. In FIG. 5, the dashed curves are for the cold-forged material before stress relief, and the solid curves are for the cold-forged material after stress relief. The cold-forged material exhibits a tensile strength curve 6a before stress relief and 6b after stress relief; a yield strength curve 7a before stress relief and curve 7b after stress relief; an elongation curve 8a before stress relief and curve 8b after; and a hardness curve 9a before stress relief and 9b after.

Hardness, strength, elongation and reduction in area are all inter-related mechanical properties. In general, as hardness and strength of the material increase, elongation and reduction in area decrease. In other words, high elongation and large reduction in area indicate a soft material with high ductility; high hardness and strength values indicate a strong material with low elongation and low reduction in area values. In light of these mechanical property interactions, the percent elongation of the new cold-forged material was high compared with other implant alloys. The geometry of the test samples of cold-forged stainless steel did not lend itself to calculations of reduction in area. However, cold-forging increased the strength without a proportionate decrease in ductility, as shown in FIG. 5.

Figure 6:
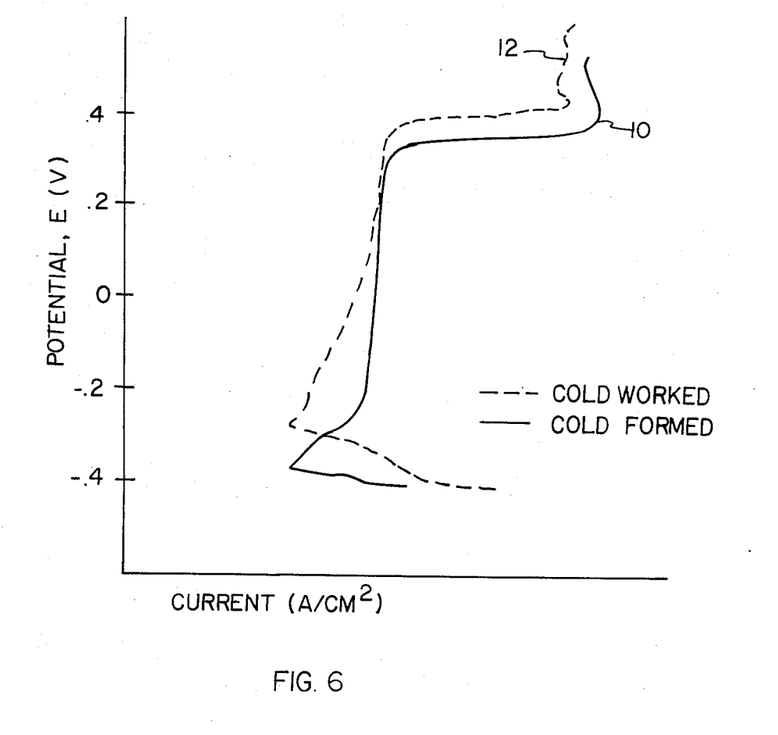
FIG. 6 is a graph showing corrosion or pitting potential for material cold-forged in accordance with the invention compared with the starting material.

FIG. 6 compares the pitting potential of the new cold-forged material, represented by solid line curve 10, compared with the pitting potential curve for the cold-worked starting material indicated as broken line curve 12. As can be seen by comparing the curves 10 and 12, there is a little change in the pitting potential for the new cold-forged material compared to the cold-worked starting material. What is known is "crevice" corrosion testing was conducted using standard techniques simulating the environment of the human body. This simulated in-vitro testing technique involves statically soaking the implant and loading it in a manner simulating its implanted condition. The tests were conducted in Ringer's solution at 37° C. and permitted an evaluation of the outer surfaces of the device for pitting, as well as internal crevice corrosion. Observation of the tested implants revealed no detectable difference between crevice corrosion testing results for the cold-forged Type 316L stainless steel and the Type 316L cold-worked starting material.

Figure 7:
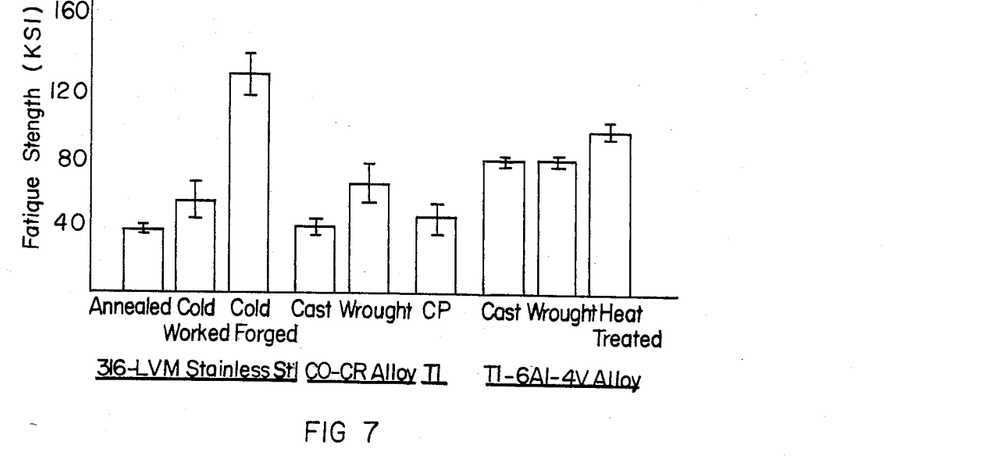
FIG. 7 is a bar graph comparing the fatigue strength for material cold-forged in accordance with the invention with previously available implant alloys.
Figure 8:
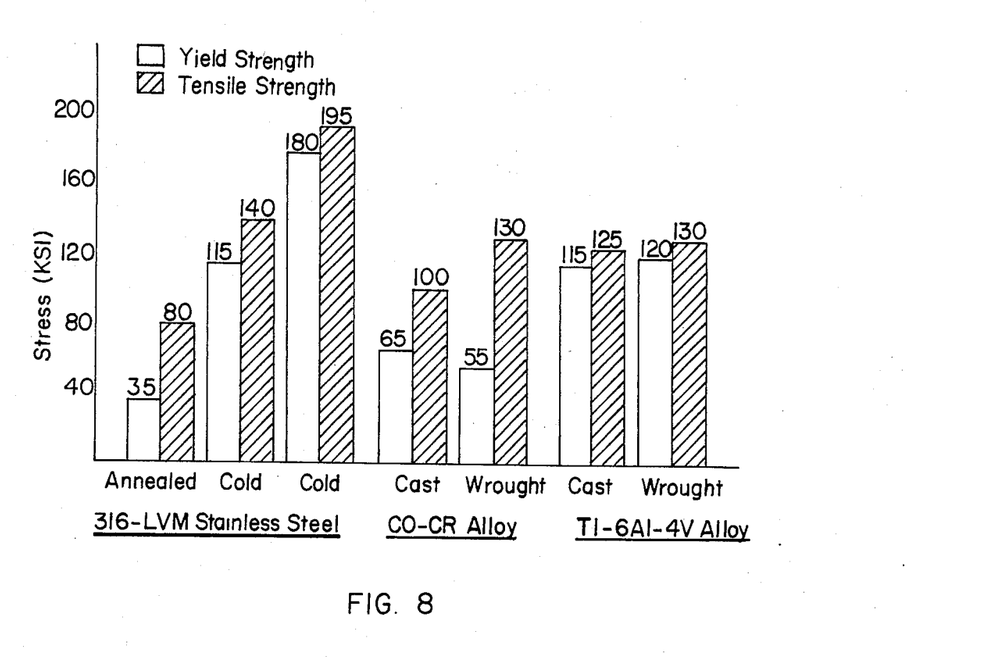
FIG. 8 is a bar graph similar to the one in FIG. 6 illustrating the yield and tensile strengths of material cold-forged in accordance with the invention.
Figure 9:
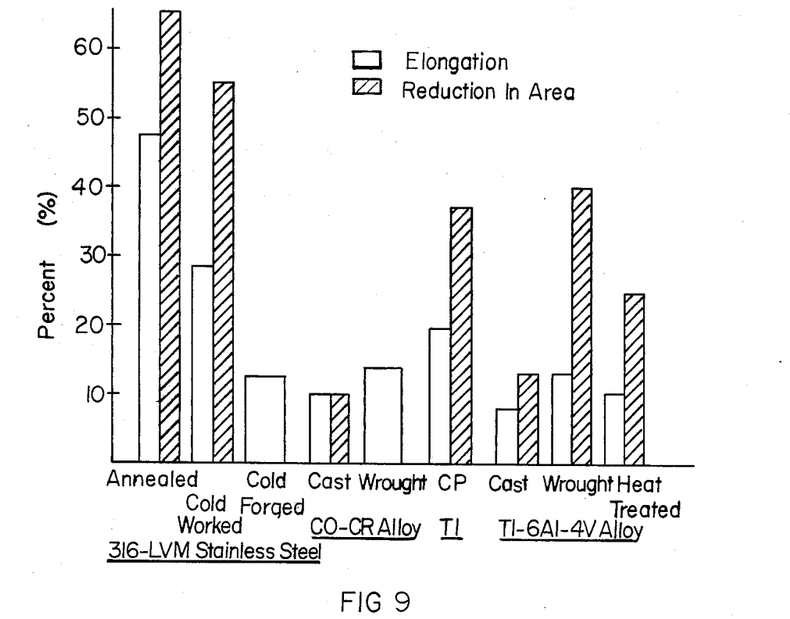
FIG. 9 is a bar graph similar to the one in FIG. 6 illustrating elongation and reduction in area values of the material cold-forged in accordance with the invention.

The bar graphs of FIGS. 7-9 compare the mechanical properties of the new cold-forged material with previously available implant materials. The fatigue strength data shown in FIG. 7 graphically illustrate the improvement in fatigue strength of the cold-forged material. A mean fatigue strength value of 120 KSI represents an improvement of about 100% over the mean value of 55 KSI for the stock cold-worked 316L starting material. In addition, this mean value of fatigue strength represents an improvement of about 25% over the highest previously available value for heat treated Ti-6A1-4V alloy of about 100 KSI.

The yield and tensile strength values shown in FIG. 8 also reflect a significant improvement over the cold-worked 316L starting material and the Ti-6Al-4V alloy. The mean tensile strength value of 195 KSI for the cold-forged material represents a 40% improvement over the 140 KSI value for the stock cold-worked material. A mean value of 180 KSI for yield strength represents about a 55% improvement over the value of 115 KSI for the yield strength for the stock cold-worked material.

Figure 10:
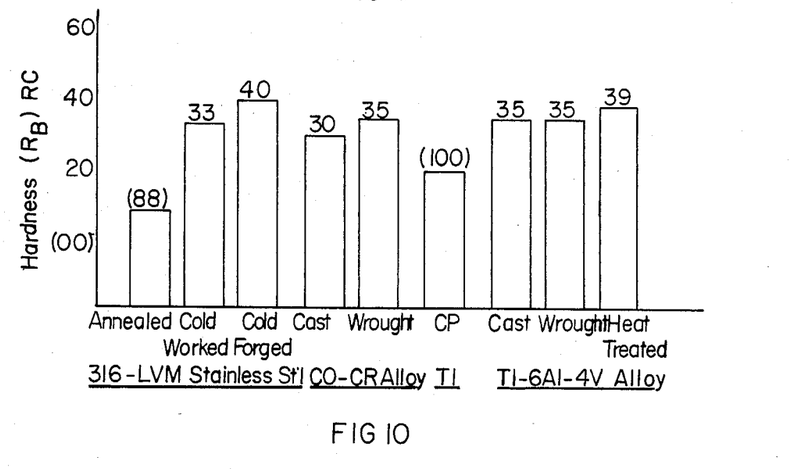
FIG. 10 is a bar graph similar to the one in FIG. 6 illustrating hardness values of the material cold-forged in accordance with the invention.

Elongation values for the implant materials are shown in FIG. 9. A decrease in the percentage of elongation was found for the cold-forged material as compared to the stock cold-worked material. Hardness values are shown in FIG. 10, which indicates that the cold-forged material has a hardness comparable to the heat treated Ti-6Al-4V alloy and somewhat better than the cold-worked 316L stainless steel.

As shown in the overall mechanical properties reflected in FIGS. 7-10, the new cold-forged material has significantly better strength characteristics than previously available implant materials. Moreover, as the stress corrosion fatigue data in FIGS. 4 and 5 reflect, the new cold-forged material has substantially better corrosion resistance properties than the starting material.

Turning to the detailed description of the cold-forging technique of the instant invention, for purposes of illustration, the technique will be described in the context of manufacturing a hip plate surgical implant. This description is presented for the purpose of illustrating a preferred method of using an austenitic stainless steel implant alloy as a starting material to manufacture a surgical implant having improved mechanical properties and corrosion resistance.

Figure 11:
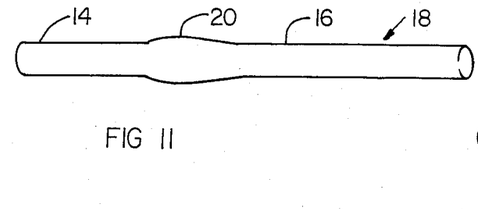
FIG. 11 is a perspective view of a piece of bar stock after the first step of a preferred cold-forging technique in accordance with the invention for manufacturing a hip plate.
Figure 12:
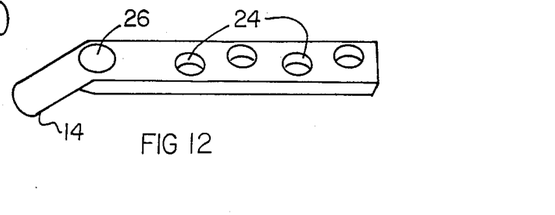
FIG. 12 is a perspective view of a completed hip plate manufactured by the preferred method of the instant invention.

Starting with an 11/16-inch (1.75 centimeters) bar of cold-worked 316L stainless steel, the bar is initially forged to the shape shown in FIG. 11. More particularly, a barrel end 14 and an opposite plate end 16 are impact reduced by an appropriate rapid reduction technique to an outside diameter of about 0.52 inches (1.32 centimeters) to form a forged bar as shown in FIG. 11. The microscopic photograph of FIG. 2 shows the microstructure of the material after this initial forging step of the cold-forging process. An intermediate portion 20 is left unforged to provide angled portion 22 of the hip plate shown in FIG. 12 with additional material thickness for greater mechanical strength.

The initially forged bar of FIG. 11 is then bent about the intermediate portion 20 to form a predetermined angle between the barrel end 14 and the plate end 16. The final configuration of the plate end 16 is formed by further forging the intermediate portion 20 and the plate end 16 by pressing with a suitably shaped die so that the final thickness of the plate end 16 is about 0.25 inch (0.635 centimeter). The pressing operation is accomplished using a pressing force of about 880 to 1102 U.S. tons (800-1000 metric tons). Thereafter, holes 24 are drilled through the hip plate, and hole 26 is drilled through the barrel end 14, which are conventional and well known in the manufacture of hip plates. The hole 26 is sized for receiving a compression screw (not shown).

In this manner, the hip plate can be formed at room temperature by relatively inexpensive cold-forging techniques to yield a surgical implant formed from a cold-worked, Type 316L stainless steel starting material, which produces a final product with better mechanical properties and corrosion resistance than has previously been possible with other manufacturing techniques.

After cold-forging the steel into the hip plate, the manufactured plate is then stress relieved by heating to a temperature of about 750° F. (399° C.) and maintaining it at that temperature for about 2 hours, followed by ambient air cooling. As shown in FIG. 5, the stress relieving step improves both the tensile strength, represented by elevation of the stress curve from the broken line curve 6a to the solid line curve 6b and the yield strength, elevated from the broken line 7a to the solid line 7b. Improvements in ductility are also shown by comparing the elongation curves 8a and 8b, which respectively reflect elongation both before and after work pieces had been stress relieved, and the hardness curves 9a and 9b, also respectively before and after stress relief.

The foregoing disclosure and description of the invention are illustrative and explanatory thereof, and various changes in the size, shape and materials, as well as in the details of the illustrated construction may be made without departing from the spirit of the invention, all of which are contemplated as falling within the scope of the invention.

What is claimed is:

1. A corrosion resistant, austenitic, stainless steel prosthetic device, adapted to be implanted in animals, and formed as a result of a method comprising the step of cold forging a starting material consisting essentially of biocompatible 316L stainless steel with a maximum carbon content of about 0.03% until it has a microstructure comprising an ASTM grain-size index above about 14 and having an absence of discernible slip planes at a magnification of about 600×.

2. The method of claim 1 wherein the cold-forging step is practiced to alter the ASTM grain-size index of the material from about 8 for the starting material to an ASTM grain-size index of about 14 or higher for the forged material.

3. The method of claim 2 wherein the starting material is a length of bar stock and the cold forging step includes:
   initially forging opposite end portions of the bar stock;
   bending the initially forged bar stock about an intermediate portion thereof; and
   further forging one end portion of the initially forged, bent stock to a predetermined shape.

4. The method of claim 3 wherein the initially forging step of the cold forging process includes a rapid reduction in diameter of the starting bar.

5. The method of claim 3 wherein the further forging step of the cold forging step includes pressing the one end portion of the stock with a shaped die.

6. The method of claim 5, further comprising the step of:
   stress relieving the forged material after the rapid reduction step, wherein the stress relieving step includes
   heating the material to the temperature of about 750° F. (399° C.); and
   maintaining the material at the temperature for about two hours, followed by ambient air cooling.

7. The method of claim 6 wherein the cold forging step is practiced to form a surgical implant.

8. The method of claim 7 wherein the surgical implant is a hip plate.

9. The method of claim 8 wherein the starting material is formed of Type 316L stainless steel.

10. The method of claim 9 wherein the pressing step includes applying a force greater than about 700 U.S. tons.

11. A method of manufacturing a surgical implant device from bar stock Type 316L stainless steel starting material below its recrystallization temperature, comprising the steps of:
   rapidly reducing opposite end portions of the starting material, leaving an intermediate portion unreduced;
   bending the reduced bar about the intermediate portion to form a predetermined angle between the opposite end portions;
   pressing one of the end portions into a suitable configuration; and
   wherein the rapid reduction and pressing steps result in the device having an ASTM grain-size index above about 14 and having an absence of discernable slip planes at a magnification of about 600×.

12. The method of claim 11, wherein the device is stress relieved after the cold forging steps.

* * * * *